United States Patent [19]
Willock

[11] 3,938,909
[45] Feb. 17, 1976

[54] SINGLE NEEDLE ALTERNATING FLOW BLOOD PUMP SYSTEM

[76] Inventor: Charles B. Willock, 16222 SE. Oatfield Road, Milwaukie, Oreg. 97222

[22] Filed: June 24, 1974

[21] Appl. No.: 482,424

Related U.S. Application Data

[62] Division of Ser. No. 348,509, April 6, 1973, Pat. No. 3,848,592.

[52] U.S. Cl. .................. 417/12; 417/412; 417/477; 251/9
[51] Int. Cl.² ..................... F04B 49/00; F04B 43/08; F04B 43/12; F04B 45/06
[58] Field of Search ........... 417/477, 476, 475, 474, 417/412, 478, 12; 251/9; 137/565.1, 565.2

[56] References Cited
UNITED STATES PATENTS

| | | | |
|---|---|---|---|
| 1,988,624 | 1/1935 | Kipp | 417/479 X |
| 3,723,030 | 3/1973 | Gelfard | 417/477 |
| 3,726,613 | 4/1973 | Casimir | 417/477 |
| 3,791,767 | 2/1974 | Shill | 417/387 |

Primary Examiner—John J. Vrablik
Assistant Examiner—Richard E. Gluck
Attorney, Agent, or Firm—Klarquist, Sparkman, Campbell, Leigh, Hall & Whinston

[57] ABSTRACT

A blood pump system, typically employed in dialysis, includes a blood pump for withdrawing blood via a single hypodermic needle and valve means operated in synchronism therewith for returning treated blood via the same hypodermic needle. The operation of the blood pump is cyclically interrupted and the valve means opened for the alternate withdrawal and return of blood.

3 Claims, 5 Drawing Figures

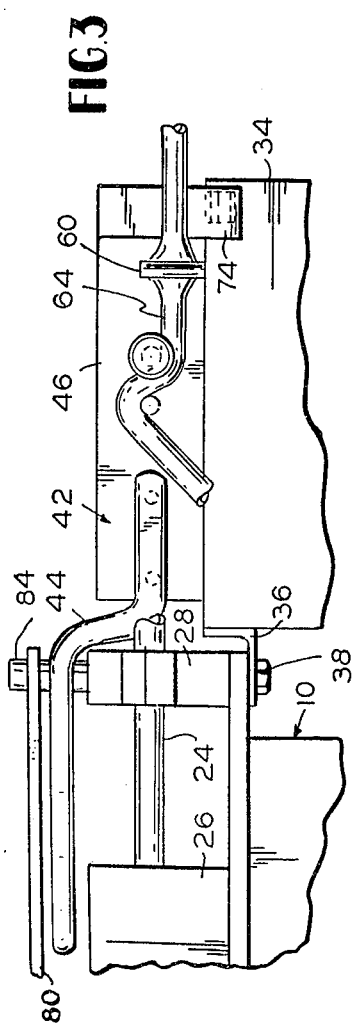
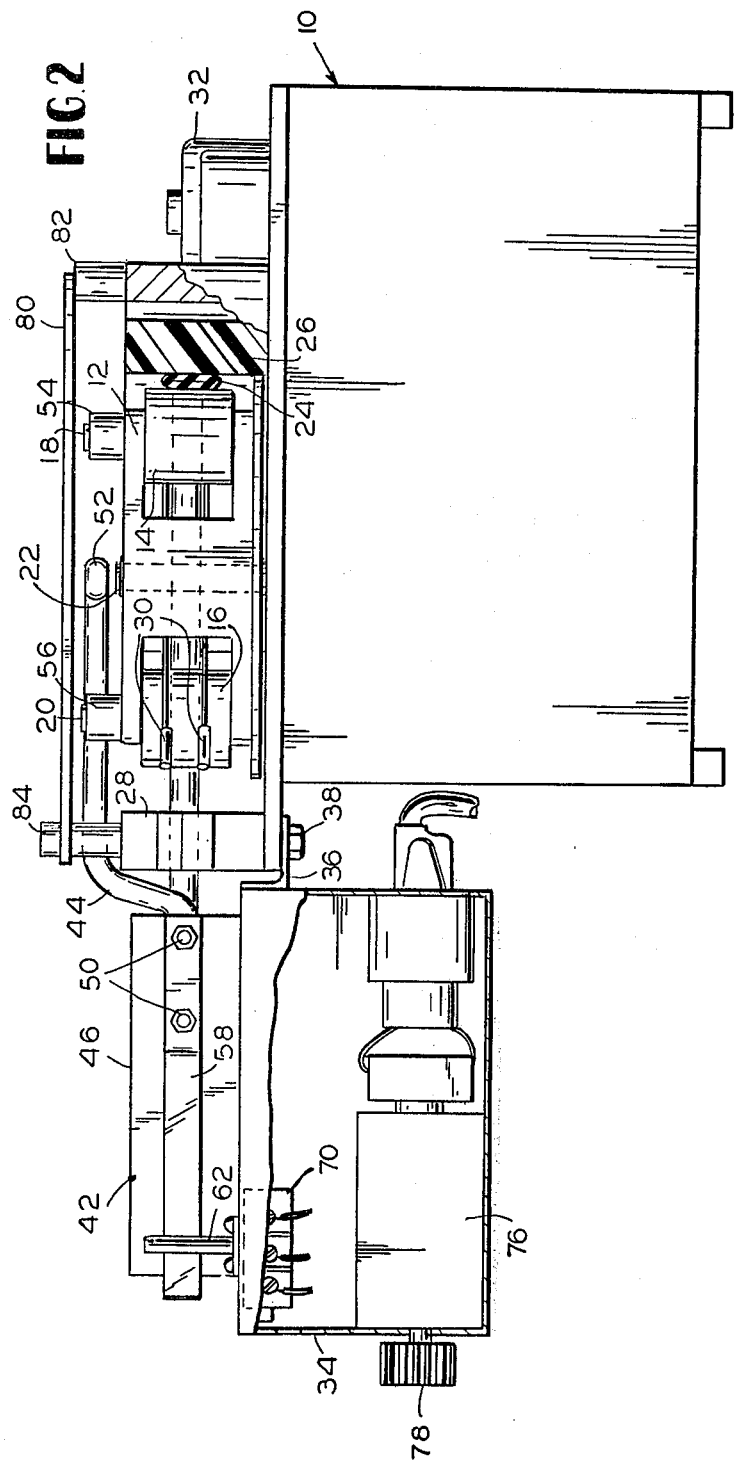

SINGLE NEEDLE ALTERNATING FLOW BLOOD PUMP SYSTEM

This is a division of application Ser. No. 348,509 filed Apr. 6, 1973, now U.S. Pat. No. 3,848,592.

BACKGROUND OF THE INVENTION

In the use of an "artificial kidney", dialysis of the patient's blood requires some means of withdrawing the blood from the patient's body and returning the same after treatment. With cannulae, providing permanent tubular connection to the patient, connection of the patient to the dialyzer apparatus is facilitated. However, a patient may not tolerate this arrangement because of infection or the like. Alternatively, plural hypodermic needles may be inserted in a patient's vein after insertion of a fistula between a vein and an artery, with one needle being utilized for withdrawal of blood while a second needle is employed to return blood to the vein. A more desirable system would avoid the requirement for repeated insertion of both needles.

A prior art single needle system withdraws and returns blood via the same hypodermic needle and includes a pair of clamp valves employed in two connections to the hypodermic needle so that blood can be alternately withdrawn and returned therethrough. In this system the valves are solenoid operated in response to pressure detected at a dialyzer output. However, pumping in such a system tends to produce a vacuum at the pump inlet, flattening the plastic tubing and causing cessation of system operation. Moreover, the addition of solenoid operated valves represents additional equipment and expense.

SUMMARY OF THE INVENTION

According to the present invention, a liquid flow loop is connected at either end to a single path such as a hypodermic needle. This loop includes pumping means for transporting liquid in the loop, and valve means for temporarily impeding the passage of liquid. The pumping means and the valve means operate synchronously for the alternate pumping and opening of the valve means, whereby liquid is alternately withdrawn and returned via the single path.

In accordance with a particular embodiment of the present invention, the pumping means comprises a blood pump for receiving blood from a single path, and means are responsive to the blood pump operation for cyclically interrupting operation thereof whereby withdrawal of blood is interrupted. At the same time, the valve means is opened for returning blood via the single path.

It is accordingly an object of the present invention to provide an improved alternating flow blood pump system and method for alternate removal of blood from a blood vessel and return to said blood vessel via a single needle.

It is a further object of the present invention to provide an improved single needle alternating flow blood pump system and method which is reliable in operation, and economical in construction.

It is a further object of the present invention to provide an improved single needle alternating flow blood pump system and method which is readily adapted to a conventional blood pump.

It is a further object of the present invention to provide an improved attachment for a conventional blood pump facilitating withdrawal and return of blood from a patient.

It is a further object of the present invention to provide an improved liquid flow system for withdrawing and returning liquid to a single flow path from and to a loop attached thereto.

The subject matter which I regard as my invention is particularly pointed out and distinctly claimed in the concluding portion of this specification. The invention however, both as to organization and method of operation together with further advantages and objects thereof, may best be understood by reference to the following description taken in connection with the accompanying drawings wherein like reference characters refer to like elements.

DRAWINGS

FIG. 2 is a partially broken away side view of the modified blood pump taken at 2—2 in FIG. 1;

FIG. 3 is a partially broken away side view of the FIG. 1 blood pump and attachment thereto according to the present invention, said view being taken at 3—3 in FIG. 1;

DETAILED DESCRIPTION

Figure 1:
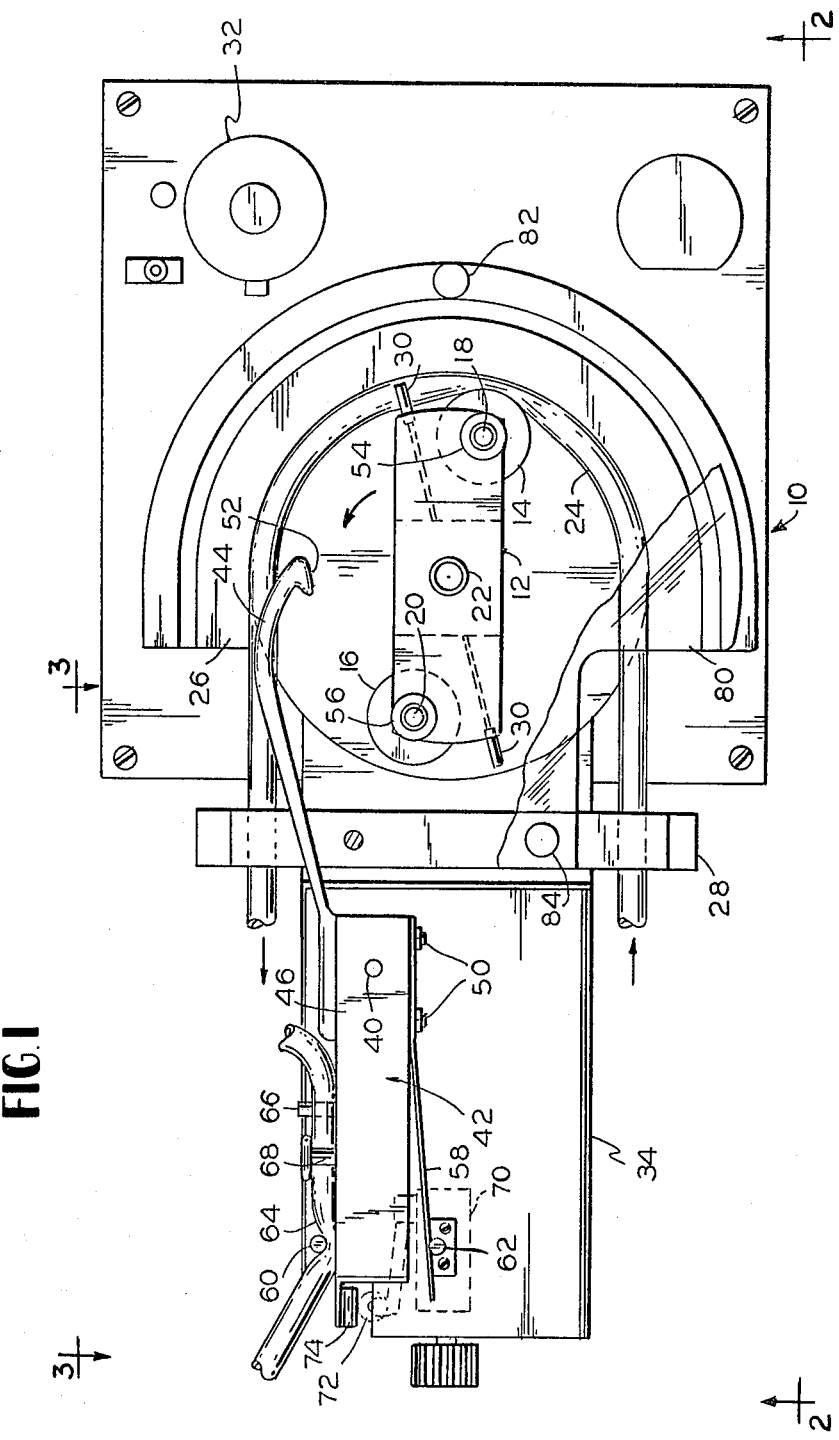
FIG. 1 is a plan view of a blood pump as modified according to the present invention.

Referring to the drawings, and particularly to FIGS. 1, 2 and 3, the system according to the present invention utilizes a conventional blood pump of the roller-and-flexible-tube type indicated at 10, said blood pump including a rotatable rotor 12 provided with rollers 14 and 16 mounted on spindles 18 and 20, respectively, at corners of the rotor. When the rotor is rotated by means of drive shaft 22, the rollers 14 and 16 alternately engage pumping segment 24 of flexible plastic tubing disposed in a semicircle around the inside of U-shaped guide 26, the pumping segment being held in position by a crossbar 28 secured to the front of the pump. As the rotor 12 rotates in a counterclockwise direction, for example, the rollers rotate around the inside of U-shaped guide 26 forcing the pumping segment against the inside wall of the U-shaped guide and pumping blood in the direction indicated by the arrows. Movable guides 30 are also suitably mounted upon rotor 12 and act to keep the pumping segment aligned in front of the rollers 14 and 16. The speed of rotor rotation is suitably controlled by an adjusting knob 32 which is operative to control the speed of the pump motor (not shown) which turns drive shaft 22.

In accordance with an aspect of the present invention, an attachment having a frame 34 may be mounted on the front of the blood pump by means of bracket 36 secured to the blood pump with bolts 38 extending through and also securing crossbar 28 to the pump. A pivot pin 40 extends upwardly from the forward part of the frame upon which an actuating arm generally indicated at 42 is rotatable. This actuating arm includes a forward portion 44 comprising a hook-shaped rod secured to a rearward block portion 46 by means of a pair of bolts 50 extending through the block portion 46 on either side of pivot pin 40. The hook-shaped rod forward portion 44 extends upwardly from the end of block 46, and over the crossbar 28 for positioning forward end 52 in the path of upper rollers 54 and 56 mounted upon spindles 18 and 20, respectively, above the conventional rollers 14 and 16. As can be seen in FIG. 1, the arm portion 44 is hooked toward the rotor drive shaft 22 and as the rotor 12 turns, the upper rollers 54 and 56 will successively engage forward end 52 of arm portion 44.

Block 46 is provided with a leaf spring 58, also secured thereto by bolts 50, which normally urges block 46 toward clamping pin 60, the latter extending upwardly from frame 34. The spring 58 bears against upwardly extending spring retaining pin 62 which may be horizontally slotted to receive the leaf spring. A section of flexible plastic tubing 64 is normally received between the body of block 46 and clamping pin 60 where it is normally compressed between the two, as illustrated, to close off the flow of liquid, i.e., blood, through tubing section 64. This portion of tubing together with elements 46 and 60 comprise a valve or clamp according to the present invention. For convenience in maintaining the proper position of tubing section 64, the same is held between a pair of horizontal pins 66 and 68 extending outwardly from block 46, the latter pin having an enlarged head for retaining the tubing section 64 in position. It will be seen that as one of the rollers 54 or 56 contacts forward end 52 of arm portion 44 and causes the arm 42 to rotate in a counterclockwise direction against the bias of spring 58, the tubing section 64 will be unclamped to a valve-open position from a valve-closed position.

Frame 34 further houses a limit switch 70 having an actuator 72 engageable by a downward extension 74 attached to block 46. Rotation of arm 42 also operates the limit switch closing its normally open contacts and opening its normally closed contacts, as hereinafter more fully described. As also hereinafter more fully described, the operation of the limit switch disconnects the blood pump whereby the blood pump rotor 24 stops rotation in a position wherein either roller 54 or roller 56 is in contact with arm portion 44. The blood pump rotor at such time will be positioned so that both rollers 14 and 16 compress pumping segment 24 at opposite sides of U-shaped guide 26 whereby the blood pump 10 effectively acts as a closed valve against the flow of blood into pumping segment 24. After a predetermined period of time, as selected by means of timer 76, power is restored to the blood pump motor and rotation of rotor 12 resumes until the next one of the upper rollers 54 or 56 contacts forward end 52 of arm portion 44. When the blood pump rotor resumes rotation, arm 42 rotates clockwise to its normal clamping position relative to tubing section 64, and limit switch actuator 72 is also returned to its initial position awaiting the turning of blood pump rotor 12 through 180° The time during which the rotor is temporarily stopped, and tubing section 64 is unclamped, is determined by the setting of timer adjustment 78. Timer 78 is conveniently a conventional electric or electronic timer and is connected as hereinafter more fully described.

The blood pump 10 is of standard construction as hereinbefore indicated but is suitably modified by upward extension of spindles 18 and 20 to support the upper rollers 54 and 56. Also, a cover 80 is raised above the level of rollers 54 and 56 by means of upper supports 82 and 84.

Figure 4:
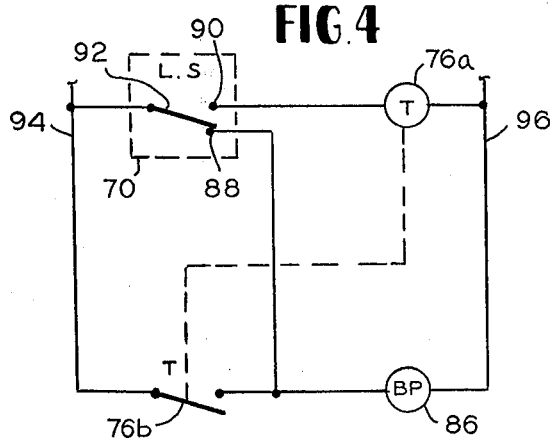
FIG. 4 is a diagram illustrating an electrical control circuit employed according to the present invention.

FIG. 4 is an electrical circuit diagram illustrating the connection of limit switch 70, timer 76, and blood pump motor 86. Limit switch 70 has a normally closed contact 88 and a normally open contact 90, these contacts providing the indicated connection until actuator 72 is moved inwardly by extension 74 of block 46, whereupon the movable contact 92 opens a circuit from power line 94 to contact 88 and closes a circuit from power line 94 to contact 90. One side of blood pump motor 86 is connected to power line 96, and until actuation of the limit switch, a circuit from the blood pump motor is also completed to power line 94 through contacts 92 and 88 bringing about motor operation and rotation of rotor 12. However, when the blood pump rotor moves to a position whereby arm 42 is rotated in a counterclockwise direction, the limit switch 70 disconnects motor 86 whereby blood pump rotor rotation is temporarily halted. At the same time, timer coil 76a of timer 76 is energized via limit switch contact 90, and at the conclusion of a preset time period operating coil 76a closes normally open contacts 76b of the timer for re-energizing blood pump motor 86, the circuit being completed from power line 94 through contacts 76b and the blood pump motor to power line 96. Thereupon, the blood pump rotor resumes rotation and the limit switch contacts resume their position illustrated in the drawing whereby blood pump motor 86 remains energized after the timer contacts reopen. The blood pump rotor will then continue rotation until the next upper roller rotates arm 42, i.e., 180° later.

Figure 5:
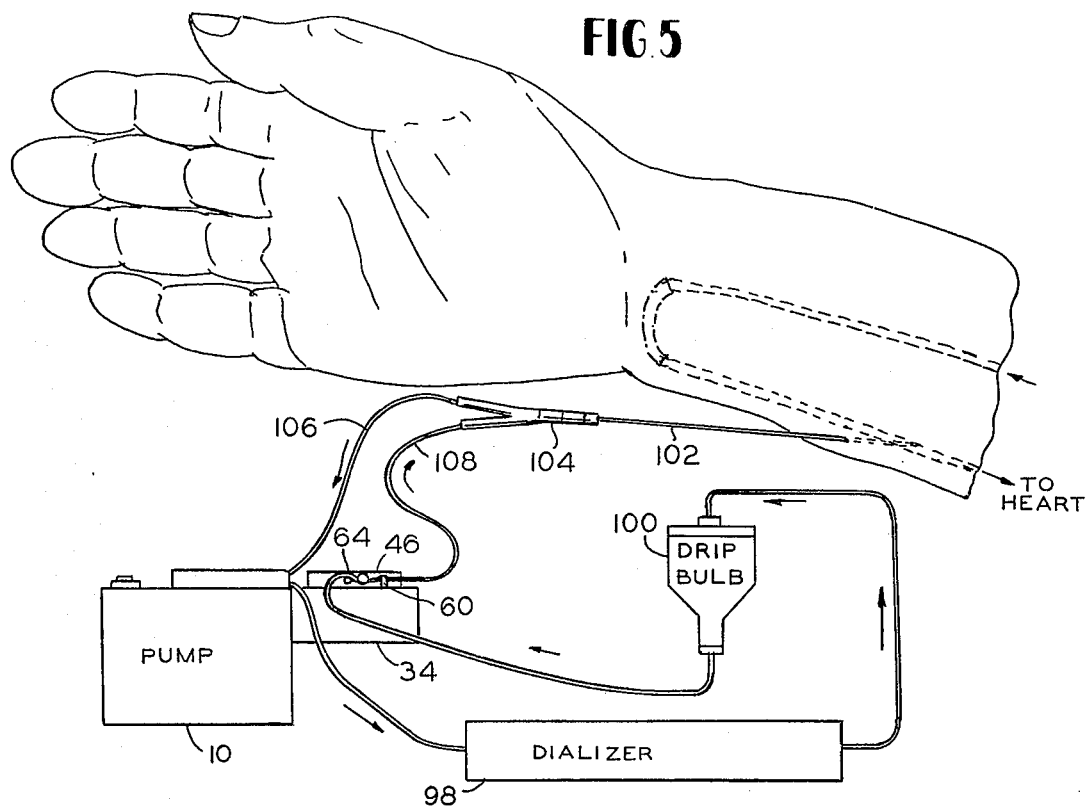
FIG. 5 is a schematic illustration of an over-all system and method according to the present invention, depicting the connection thereof to a patient.

The over-all system and method according to the present invention is illustrated in FIG. 5 wherein the blood pump and attachment are employed in a blood flow loop including the pump, a blood receiving or treatment means typically comprising a dialyzer 98, a drip bulb 100, and a valve or clamp comprising block 46 and clamping pin 60 between which tubing section 64 is received. A blood flow loop comprising a blood set alternately withdraws blood from a single path comprising a hypodermic needle 102, drawing the blood through the blood pump and into the dialyzer, and then expelling blood into the hypodermic needle as the valve 46, 60 opens. Common connection with both ends of the blood flow loop and the hypodermic needle is made by Y connection means 104.

The blood receiving means 98 comprising a dialyzer or the like is capable of receiving pressure as the membrane thereof expands slightly such that blood is forced into the hypodermic needle when valve 46, 60 opens. Thus, blood is drawn from the hypodermic needle through tubing portion 106 and delivered to the dialyzer as the pump rotor rotates through 180°. At this time, the pump rotor stops through the action of arm 42 and limit switch 70, while valve or clamp 46, 60 opens returning blood to the hypodermic needle via tubing portion 108. At such time, the blood pump rollers 14 and 16 themselves prevent the flow of blood through tubing portion 106 in the direction of the pump, i.e., the pump acts as the clamp or valve. After a predetermined time, governed according to the timer 76, the pump resumes rotation and valve 46, 60 is re-closed so that blood is once again withdrawn from the hypodermic needle. In a typical instance, the timing of timer 76 and the speed of rotation of the blood pump are adjusted so that the time of rotation of the pump rotor through 180° is approximately one-half second, and the temporary interruption in blood pump operation is also approximately one-half second.

The hypodermic needle 102 may be inserted in an arm vein of a patient provided with a fistula by operative procedure, the latter causing expansion of the vein and allowing easier insertion of the hypodermic needle. The hypodermic needle, which may comprise a 14-gauge needle, is inserted in the direction of blood flow. Typically, the patient must undergo periodic dialysis and thus must reinsert the hypodermic needle at frequent intervals. The system and method according to the present invention permits the insertion of only one hypodermic needle, rather than two as in the case of the more conventional procedure, and is of appreciable advantage from the patient's point of view. The present system can also effect 200 cc per minute transfer of blood. The system according to the present invention, wherein blood is alternately withdrawn from the vein of the patient and returned through a single hypodermic needle, and wherein such withdrawal and return are synchronized primarily according to the operation of the blood pump, is preferable to a system wherein a pump is continuously operated since in the latter instance undesired vacuum then produced on the input side of the pump may cause tube flattening or the like. Moreover, the present system does not require additional solenoid operated clamps or pressure gauge control therefor but advantageously functions in response to the cyclical operation of the blood pump itself, or in synchronism therewith.

While I have shown and described the preferred embodiment of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. In blood pump including a guide for receiving a liquid-carrying tube, a rotor carrying rollers for bearing against said tube, and rotor drive means for rotating said rotor, the improvement comprising an attachment for said pump adapting said pump for use in a system for alternately withdrawing and returning blood via a single path, said attachment including:

mounting means for attachment relative to said blood pump, an actuating arm pivotable with respect to said mounting means and having a first portion disposed in a path generated by a portion of said rotor whereby rotation of said rotor to a predetermined position pivots said arm from a first position to a second position, a spring normally biasing said arm into said first position to be actuated by said rotor, a clamping member disposed adjacent said arm and receiving a length of tubing between said arm and said clamping member such that said arm in its first position compresses said tubing against said clamping member and in said second position unclamping said tubing, said tubing communicating with said liquid-carrying tube, switching means operated by movement of said arm to said second position, said switching means being connected for interrupting power to said drive means for said pump, whereby said arm is effective for unclamping said tubing while said power is interrupted, and means for subsequently restoring power to said drive means for reinitiating pumping by said pump.

2. The apparatus according to claim 1 wherein said means for subsequently restoring power to said drive means comprises a timer also actuated by said switching means for restoring power to said drive means after a predetermined period of time.

3. The apparatus according to claim 1 wherein said portion of said rotor comprises upward extensions proximate said rollers for contacting said actuating arm.

* * * * *